United States Patent
Hwang et al.

(10) Patent No.: US 7,785,549 B2
(45) Date of Patent: Aug. 31, 2010

(54) RECYCLING SYSTEM FOR HYDROXYLAMINE FORMATION AND OXIMATION

(75) Inventors: Jih-Dar Hwang, Taipei (TW); Hsiu-Li Cheng, Taipei (TW); Shou-Li Luo, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 443 days.

(21) Appl. No.: 11/900,385

(22) Filed: Sep. 11, 2007

(65) Prior Publication Data

US 2008/0167495 A1    Jul. 10, 2008

(30) Foreign Application Priority Data

Jan. 5, 2007    (TW) .............................. 96100435 A

(51) Int. Cl.
*B01J 8/00* (2006.01)
*B01J 8/04* (2006.01)
*C07C 259/00* (2006.01)

(52) U.S. Cl. .................. 422/234; 422/189; 564/253; 564/259; 564/262

(58) Field of Classification Search .................. 422/189, 422/234; 564/253, 259, 262
See application file for complete search history.

(56) References Cited

U.S. PATENT DOCUMENTS

| 4,025,426 A | * | 5/1977 | Anderson et al. ........... 210/662 |
| 2005/0070739 A1 | * | 3/2005 | Benneker et al. ............ 564/259 |

* cited by examiner

*Primary Examiner*—Walter D Griffin
*Assistant Examiner*—Lessanework Seifu
(74) *Attorney, Agent, or Firm*—Edwards Angell Palmer & Dodge LLP; Peter F. Corless; Dwight D. Kim

(57) ABSTRACT

A recycling system for hydroxylamine formation and oximation is proposed. The recycling system includes a hydroxylamine formation zone, an oximation zone, a purification zone, and an adjusting zone having a nitrate absorption tower. An inorganic process solution, used by the recycling system, partially enters the nitrate absorption tower supplementing nitrate, followed by mixing with the residual inorganic process solution, thereby reducing the loss rate of hydroxylamine in the inorganic process solution due to degradation. In addition, the organic impurities with high boiling point in the inorganic process solution can be effectively removed in the purification zone. As a result, the reduced activity or selectivity of the catalyst for hydroxylamine formation, caused by the toxic effects of these organic impurities on the catalyst, can be avoided, and hence, a high concentration of hydroxylamine can be obtained.

6 Claims, 3 Drawing Sheets

RECYCLING SYSTEM FOR HYDROXYLAMINE FORMATION AND OXIMATION

FIELD OF THE INVENTION

The present invention relates to recycling systems for hydroxylamine formation and oximation, and, more particularly, to a recycling system for hydroxylamine formation and oximation that facilitates the production of a high concentration of hydroxylamine phosphate.

BACKGROUND OF THE INVENTION

In industry, the production of hydroxylamine is usually coupled with other processes in which hydroxylamine is usually recycled for use. One example is a recycling system for hydroxylamine formation and oximation, in which an aqueous solution of a phosphate salt is used as the inorganic process solution; hydroxylamine is formed in a hydroxylamine formation zone by reducing nitrate with hydrogen gas in the presence of a catalyst in the inorganic process solution; and then the hydroxylamine is subjected to an oximation reaction with cyclohexanone to form cyclohexanone oxime. After oximation, the inorganic process solution forms nitrate ions by adding nitric acid or adsorbing $NO_2$ (which forms nitric acid in the aqueous medium), and then the inorganic process solution is recycled to the hydroxylamine formation zone. The reactions involved in the above system are as follows:

Production of Hydroxylamine Phosphate

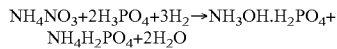
$$NH_4NO_3 + 2H_3PO_4 + 3H_2 \rightarrow NH_3OH.H_2PO_4 + NH_4H_2PO_4 + 2H_2O$$

Production of Cyclohexanone Oxime

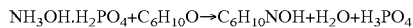
$$NH_3OH.H_2PO_4 + C_6H_{10}O \rightarrow C_6H_{10}NOH + H_2O + H_3PO_4$$

Supplementation of Nitrate Ions in the Inorganic Process Solution Containing a Phosphate Salt

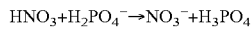
$$HNO_3 + H_2PO_4^- \rightarrow NO_3^- + H_3PO_4$$

FIG. 1 is a simplified block diagram of the conventional recycling system for hydroxylamine formation and oximation. The conventional recycling system for hydroxylamine formation and oximation, as shown in FIG. 1, comprises a hydroxylamine formation tower (10), an oximation tower (30), an extraction tower (50), a stripping tower (70) and a nitric acid absorption tower (90). In the system, a phosphate-containing inorganic process solution comprising nitrate ions, and hydrogen gas are delivered respectively via lines 101 and 103 to the hydroxylamine formation tower (10), in which hydroxylamine phosphate is synthesized. Unreacted hydrogen gas and other gases formed are discharged via a discharge line 105. The inorganic process solution containing hydroxylamine phosphate is delivered via a line 111 to the top of the oximation tower (30), and an organic solution containing cyclohexanone is delivered via lines 113 and 115 to the bottom of the oximation tower (30). The two solutions flowing in the opposite directions mix with each other and undergo oximation. The organic phase containing the produced cyclohexanone oxime is discharged from the top of the oximation tower (30) via a yield line 117, and the residual inorganic process solution is discharged from the bottom of the oximation tower (30) via a line 119. The discharged inorganic process solution is delivered via the line 119 to an extraction tower (50), in which the residual cyclohexanone oxime is removed, and then the inorganic process solution is delivered via a line 125 to a stripping tower (70), in which the residual organic impurities are removed. Finally, the stripped inorganic process solution is delivered via a line 129 to a nitric acid absorption tower (90), in which the inorganic process solution is supplemented with nitrate ions, and then the inorganic process solution is recycled to the hydroxylamine formation tower (10) for use in the hydroxylamine phosphate synthesis in the next cycle.

In the recycling system for hydroxylamine formation and oximation, after oximation of cyclohexanone with hydroxylamine is completed, the inorganic process solution discharged from the oximation tower may have residual organic impurities, which may adversely affect the reaction system. First, the organic impurities in the inorganic process solution may have a toxic effect on the catalyst for use in hydroxylamine formation, resulting in reduced activity and selectivity of the catalyst; and, as a result, the concentration and the yield of hydroxylamine cannot be effectively optimized. Moreover, when the inorganic process solution containing residual organic impurities is fed to the nitric acid absorption tower, the waste gas formed therefrom is liable to cause corrosion to the contacting materials. Therefore, finding a way to reduce the organic impurities in the inorganic process solution is a key goal in the production of high concentrations of hydroxylamine.

U.S. Pat. No. 3,997,607 discloses a method to reduce organic impurities in inorganic process solution by use of a thermal treatment. However, the waste gas formed during the thermal treatment is liable to cause corrosion to the contacting materials. Furthermore, in the case that the temperature of the thermal treatment is elevated to further reduce the total carbonyl content of the inorganic process solution, condensation between the organic matters may occur. As a result, the inorganic process solution becomes yellow, and, in addition, it becomes more difficult to remove the organic impurities from the inorganic process solution.

In another aspect, when the inorganic process solution is supplemented with nitrate ions in the nitric acid absorption tower, the residual hydroxylamine in the inorganic process solution may be degraded, causing loss of the useful hydroxylamine. Therefore, for the production of cyclohexanone oxime by using a high concentration of hydroxylamine phosphate, it is desirable to develop a recycling system for hydroxylamine formation and oximation that can effectively remove the organic impurities in the inorganic process solution and, at the same time, avoid degradation of residual hydroxylamine in the inorganic process solution.

SUMMARY OF THE INVENTION

An objective of the present invention is to provide a recycling system for hydroxylamine formation and oximation.

Another objective of the present invention to provide a recycling system for hydroxylamine formation and oximation, in which the content of the organic impurities in the inorganic process solution discharged from the oximation tower can be reduced.

Yet another objective of the present invention is to provide a recycling system for hydroxylamine formation and oximation, in which the loss of the residual hydroxylamine due to degradation can be reduced when the inorganic process solution is supplemented with nitrate ions.

In order to achieve the above and other objectives, the present invention provides a recycling system for hydroxylamine formation and oximation, comprising:

(a) a hydroxylamine formation zone, in which nitrate is reduced to hydroxylamine with a hydrogen gas in the presence of a catalyst in an inorganic process solution containing an acidic buffering agent;

(b) an oximation zone, in which hydroxylamine formed in the hydroxylamine formation zone and cyclohexanone are subjected to an oximation reaction to form cyclohexanone oxime;

(c) a purification zone, in which the organic impurities in the inorganic process solution are removed; and (d) an adjusting zone comprising a nitric acid absorption tower in which the inorganic process solution is supplemented with nitrate ions; in which the inorganic process solution fed into the adjusting zone comprises a first portion which is fed to the nitric acid absorption tower and a second portion which is not fed to the nitric acid absorption tower, and the volume of the first portion of the inorganic process solution does not exceed 20% (by volume) of the total volume of the inorganic process solution; and, the first portion of the inorganic process solution, after being supplemented with nitrate ions in the nitric acid absorption tower, is mixed with the second portion of the inorganic process solution.

According to the present invention, the loss rate of hydroxylamine in the inorganic process solution due to degradation can be reduced. In addition, organic impurities with a high boiling point in the inorganic process solution can be effectively removed in the purification zone; therefore, the reduced activity or selectivity of the catalyst for hydroxylamine formation caused by the toxic effects of these organic impurities on the catalyst can be avoided, and a high concentration of hydroxylamine can be obtained.

DETAILED DESCRIPTION OF THE INVENTION

The term "total organic carbon content" herein means that the total concentration of organic substances calculated by carbon, based on the total weight of the inorganic process solution.

Figure 1:
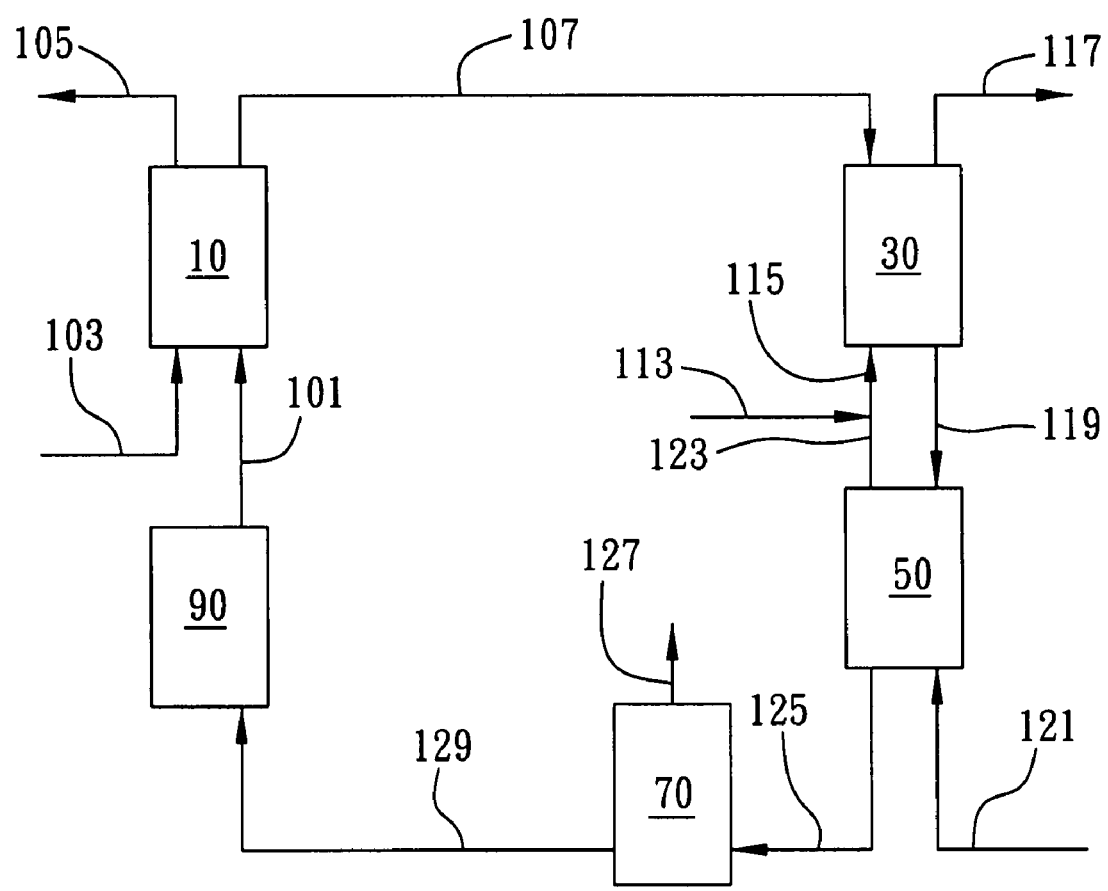
FIG. 1 is a simplified block diagram of the conventional recycling system for hydroxylamine formation and oximation.
Figure 2:
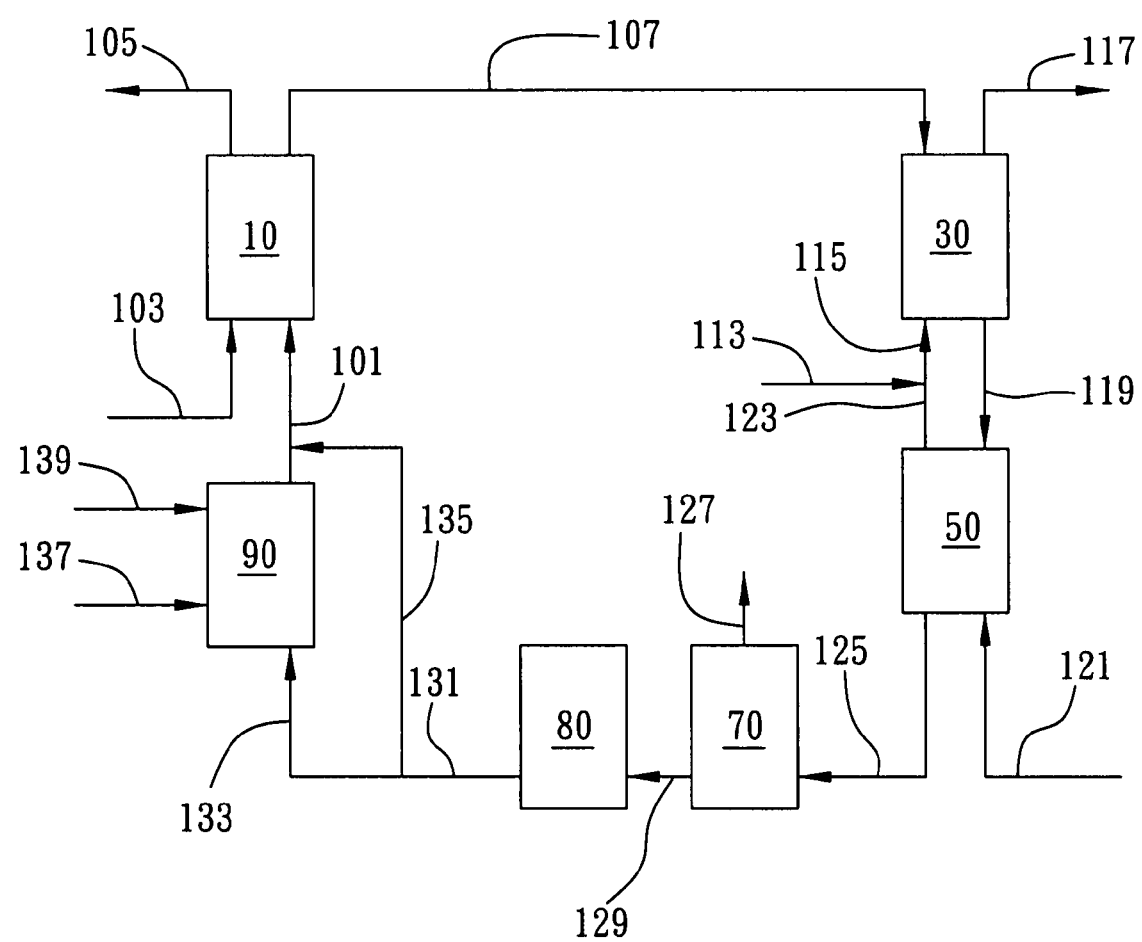
FIG. 2 is a simplified block diagram of the recycling system for hydroxylamine formation and oximation according to the first embodiment of the present invention.

FIG. 2 is a simplified block diagram of the recycling system for hydroxylamine formation and oximation according to the first embodiment of the present invention. In the first embodiment, the system comprises a hydroxylamine formation zone provided with a hydroxylamine formation tower (10); an oximation zone provided with an oximation tower (30); a purification zone including an extraction tower (50), a stripping tower (70), and an activated carbon adsorption tank (80); and an adjusting zone provided with a nitric acid absorption tower (90).

Phosphoric acid is used as the acidic buffering agent in the inorganic process solution (hereinafter, "inorganic process solution containing acidic buffering agent" may be abbreviated as "inorganic process solution"). An inorganic process solution containing 2.80 mol/kg or more hydrogen ions, 2.4 mol/kg or more phosphate salts and 0.2 mol/kg or more free nitric acid as well as a hydrogen gas are delivered respectively via lines 101 and 103 to a hydroxylamine formation tower (10), in which nitrate is reduced to hydroxylamine with a hydrogen gas by the catalysis of a noble metal catalyst, such that an inorganic process solution containing a high concentration (1.00 mol/kg or more) of hydroxylamine is obtained. The unreacted hydrogen gas and other gases formed are discharged via a line 105.

The inorganic process solution containing high concentration of hydroxylamine is delivered from the hydroxylamine formation tower (10) to the oximation zone via a line 107, and fed to the top of the oximation tower (30). An organic solution containing cyclohexanone is fed to the bottom of the oximation tower (30) via lines 113 and 115, and then contacted with the above inorganic process solution containing a high concentration of hydroxylamine from the opposite direction. Both are subjected to an oximation reaction, preferably at a temperature of 40 to 60° C. and at atmospheric, subatmospheric, or superatmospheric pressure. After completion of oximation, the organic phase containing cyclohexanone oxime is discharged from the top of the oximation tower (30) via a line 117. The concentration of cyclohexanone oxime in the organic phase is about 25% by weight (wt. %) or more, and preferably 35 wt. % or more. Residual inorganic process solution is discharged from the oximation tower (30) as described below.

The inorganic process solution discharged from the oximation tower (30) is fed via a line 119 to the purification zone including an extraction tower (50), a stripping tower (70), and an activated carbon adsorption tank (80), to remove organic impurities, including ketones, oximes, carboxylic acids and amines. In the extraction tower (50). Toluene, which is used as a solvent in the extraction tower (50), is fed via a line 121 to the extraction tower (50). The inorganic process solution discharged from the oximation tower (30) is extracted with toluene, thereby removing the residual cyclohexanone oxime. After extraction, the organic phase is delivered back to the oximation tower (30) via a line 123, and the inorganic process solution (aqueous phase) is discharged from the bottom of the extraction tower (50).

The inorganic process solution discharged from the bottom of the extraction tower (50) is delivered via a line 125 to a stripping tower (70), in which cyclohexanone produced from hydrolysis of cyclohexanone oxime together with other organic substances having lower boiling point are stripped out of the inorganic process solution and discharged from the stripping tower (70) via a line 127. After stripping, the inorganic process solution is delivered via a line 129 to the activated carbon absorption tank (80), in which the organic impurities having high boiling points are adsorbed by activated carbon and removed from the inorganic process solution.

The inorganic process solution, which is subjected to extraction, stripping and adsorption by activated carbon in the purification zone, has a total carbon content as low as 0.02 wt. % or less, preferably 0.015 wt. % or less, and more preferably 0.01 wt. %.

The purified inorganic process solution thus obtained is then delivered via a line 131 to the adjusting zone, in which the inorganic process solution is divided into two portions: a first portion which is fed to the nitric acid absorption tower (90), and a second portion which is not fed to the nitric acid absorption tower (90). In this embodiment, ammonia and air are introduced to the nitric acid absorption tower (90) respectively via a line 137 and a line 139 to prepare nitric acid in situ. Alternatively, nitric acid may be directly introduced into the nitric acid absorption tower (90) instead of preparation of nitric acid in situ. The volume of the first portion of the inorganic process solution does not exceed 20% (by volume), and preferably does not exceed 15% (by volume), of the total volume of the inorganic process solution. The first portion of the inorganic process solution is fed via a line 133 to the nitric acid absorption tower (90), in which the inorganic process solution is supplemented with nitrate ions to compensate the nitrate consumed in oximation. The first portion of the inorganic process solution, after its composition is adjusted as stated above, is discharged from the nitric acid absorption tower (90) via a line 101 and mixed with the second portion of the inorganic process solution delivered via a line 135. The mixture of these two portions are then delivered back to the hydroxylamine formation tower (10) via the line 101, for use in hydroxylamine phosphate synthesis in the next cycle.

In this embodiment, the inorganic process solution recycled back to the hydroxylamine formation tower (10) contains 0.02 to 0.08 mol/kg of hydroxylamine phosphate. The loss rate per cycle of hydroxylamine due to degradation in the nitric acid absorption tower (90) is about 1.0 mol % or less, and preferably 0.5 mol % or less, based on the total moles of hydroxylamine produced in the hydroxylamine formation tower (10). Furthermore, the composition of the inorganic process solution recycled back to the hydroxylamine formation tower (10) not only meets the requirements for the feed of the hydroxylamine formation tower (10), namely, 2.80 mol/kg or more of hydrogen ions, 2.4 mol/kg or more of phosphate salts, and 0.2 mol/kg or more of free nitric acid, but also has a low amount of organic impurities; therefore, it can be advantageously used in the production of hydroxylamine phosphate at high concentration, for example, 1.00 mol/kg or more, more preferably 1.15 mol/kg or more, still more preferably 1.3 mol/kg or more, and most preferably 1.5 mol/kg or more.

Figure 3:
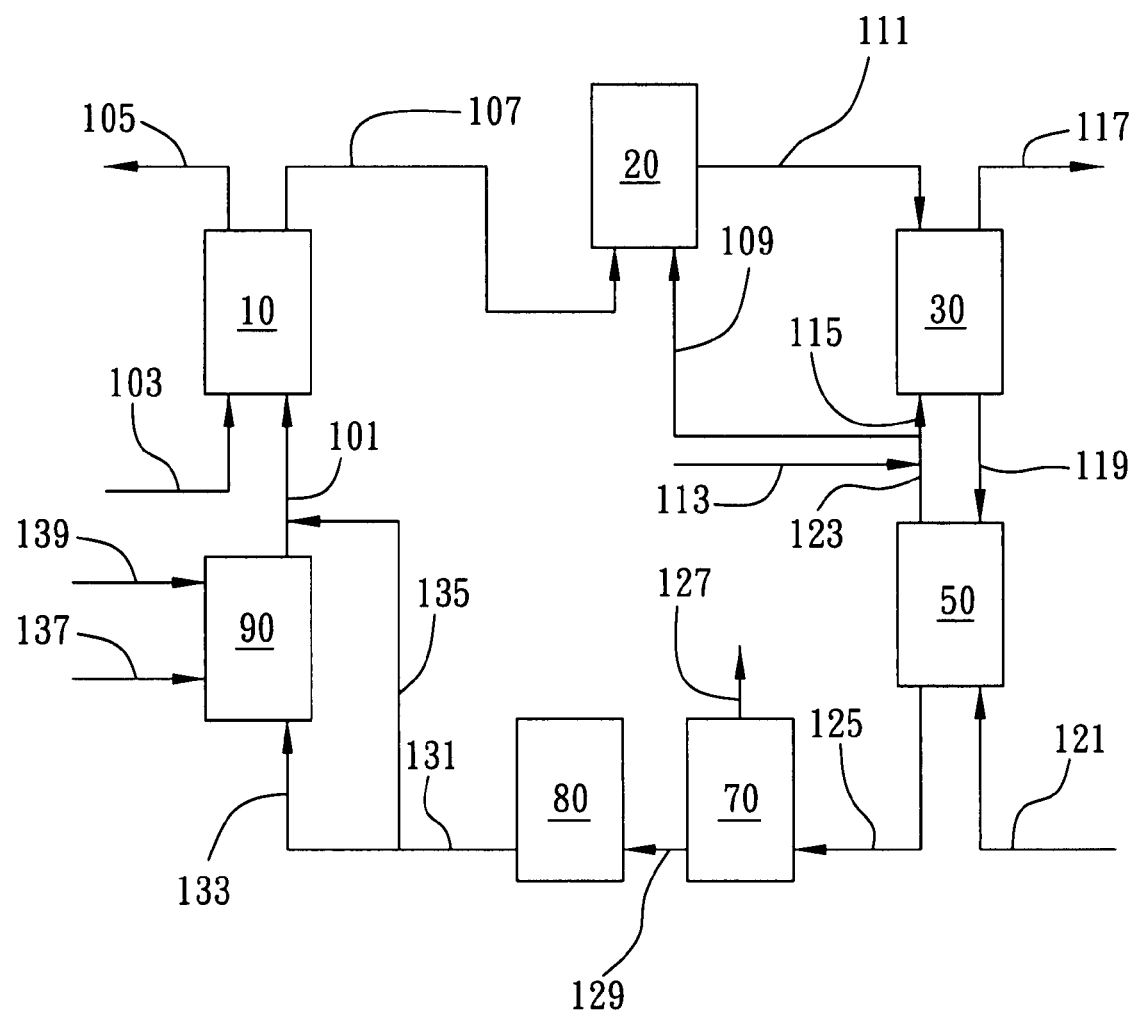
FIG. 3 is a simplified block diagram of the recycling system for hydroxylamine formation and oximation according to the second embodiment of the present invention.

FIG. 3 is a simplified block diagram of the recycling system for hydroxylamine formation and oximation according to the second embodiment of the present invention, in which same elements are represented by the same reference numbers as in the first embodiment. In the second embodiment, the system comprises a hydroxylamine formation zone provided with a hydroxylamine formation tower (10); a pre-mixing tank (20); an oximation zone provided with an oximation tower (30); a purification zone including an extraction tower (50), a stripping tower (70) and an activated carbon adsorption tank (80); and an adjusting zone provided with a nitric acid absorption tower (90).

An inorganic process solution containing 2.80 mol/kg or more of hydrogen ions, 2.4 mol/kg or more of phosphate salts, and 0.2 mol/kg or more of free nitric acid as well as a hydrogen gas are delivered respectively via lines 101 and 103 to a hydroxylamine formation tower (10), in which nitrate is reduced to hydroxylamine with a hydrogen gas in the catalysis by a noble metal catalyst, and an inorganic process solution containing high concentration (1.00 mol/kg or more) of hydroxylamine is obtained. The unreacted hydrogen gas and other gases formed are discharged via a line 105.

The inorganic process solution containing a high concentration of hydroxylamine and an organic solution of cyclohexanone, which both come from the same direction, are delivered respectively via a line 107 and a line 109 to the pre-mixing tank (20). In the pre-mixing tank (20), both solutions are pre-mixed at a temperature of 30 to 50° C. to form a reaction mixture. The concentration of hydroxylamine in the reaction mixture is reduced to 80% or less, preferably 75% or less, more preferably 65% or less, even more preferably 55% or less, and most preferably 50% or less, relative to its initial concentration, thereby increasing the efficiency of subsequent oximation reaction. The organic solution of cyclohexanone includes cyclohexanone and an organic solvent, which is, for example, but not limited to, benzene, toluene, xylene, methyl cyclopentane, cyclohexane and a mixture thereof.

The pre-mixed reaction mixture is fed to the oximation zone via a line 111, and fed to the top of the oximation tower (30) in the oximation zone. The organic solution containing cyclohexanone is fed to the bottom of the oximation tower (30) via lines 113 and 115 and contacted with the above inorganic process solution containing a high concentration of hydroxylamine fed into the oximation tower (30) from the opposite direction. Both are subjected to an oximation reaction, preferably at a temperature of 40 to 60° C. and at atmospheric, subatmospheric or superatmospheric pressure. After completion of oximation, the organic phase containing cyclohexanone oxime is discharged from the top of the oximation tower (30) via a line 117. The concentration of cyclohexanone oxime in the organic phase is about 30 wt. % or more, preferably 35 wt. % or more, and most preferably 40 wt % or more. Residual inorganic process solution is discharged from the oximation tower (30) via a line 119.

Inorganic process solution is discharged from the oximation tower (30) and fed to the purification zone including an extraction tower (50), a stripping tower (70), and an activated carbon adsorption tank (80). Toluene, which is used as a solvent in the extraction tower (50), is fed via a line 121 to the extraction tower (50), where the inorganic process solution discharged from the oximation tower (30) is extracted with the toluene, thereby removing the residual cyclohexanone oxime. After extraction, the organic phase is delivered back to the oximation tower (30) via a line 123, and the inorganic process solution (aqueous phase) is discharged from the bottom of the extraction tower (50).

The inorganic process solution discharged from the bottom of the extraction tower (50) is delivered via a line 125 to a stripping tower (70), where cyclohexanone produced from hydrolysis of cyclohexanone oxime, together with other organic substances having lower boiling points, are stripped out of the inorganic process solution and discharged from the stripping tower (70) via a line 127. After stripping, the inorganic process solution is delivered via a line 129 to the activated carbon absorption tank (80), where organic impurities having high boiling points are adsorbed by activated carbon and removed from the inorganic process solution.

The inorganic process solution, which is subjected to extraction, stripping, and adsorption by activated carbon in the purification zone, has a total carbon content as low as 0.02 wt. % or less, preferably 0.015 wt. % or less, and more preferably 0.01 wt. %.

The purified inorganic process solution thus obtained is then delivered via a line 131 to the adjusting zone, in which the inorganic process solution is divided into two portions: a first portion which is fed to the nitric acid absorption tower (90), and a second portion which is not fed to the nitric acid absorption tower (90). In this embodiment, ammonia and air are introduced to the nitric acid absorption tower (90) respectively via a line 137 and a line 139 to prepare nitric acid in situ. Alternatively, nitric acid may be directly introduced into the nitric acid absorption tower (90) instead of preparation of nitric acid in situ. The volume of the first portion of the inorganic process solution does not exceed 20% (by volume), and preferably does not exceed 15% (by volume) of the total volume of the inorganic process solution. The first portion of the inorganic process solution is fed via a line 133 to the nitric acid absorption tower (90), in which the inorganic process solution is supplemented with nitrate ions to compensate the nitrate that consumed in oximation. The first portion of the inorganic process solution, after its composition is adjusted as stated above, is discharged from the nitric acid absorption tower (90) via a line 101 and mixed with the second portion of the inorganic process solution delivered via a line 135. The mixture of these two portions are then delivered back to the hydroxylamine formation tower (10) via the line 101, for use in the hydroxylamine phosphate synthesis in the next cycle.

In this embodiment, the inorganic process solution recycled back to the hydroxylamine formation tower (10) contains 0.02 to 0.08 mol/kg of hydroxylamine phosphate. The loss rate per cycle of hydroxylamine due to degradation in the nitric acid absorption tower (90) is about 1.0 mol % or less, and preferably 0.5 mol % or less, based on the total moles of hydroxylamine produced in the hydroxylamine formation tower (10). Furthermore, the composition of the inorganic process solution recycled back to the hydroxylamine formation tower (10) not only meets the requirements for input to the hydroxylamine formation tower (10), namely, containing 2.80 mol/kg or more of hydrogen ions, 2.4 mol/kg or more of phosphate salts, and 0.2 mol/kg or more of free nitric acid, but also has a low content of organic impurities; therefore, it can be advantageously used in production of hydroxylamine phosphate at a high concentration, for example, 1.00 mol/kg or more, preferably 1.15 mol/kg or more, more preferably 1.3 mol/kg or more, and most preferably 1.5 mol/kg or more.

In the recycling system for hydroxylamine formation and oximation according to the present invention, an inorganic process solution containing phosphate salts is used as the aqueous reaction medium through the whole reaction cycle. Hydroxylamine phosphate is synthesized in a hydroxylamine formation tower by reducing nitrate with a hydrogen gas, then delivered to an oximation tower, where hydroxylamine phosphate and cyclohexanone are subjected to an oximation reaction to form cyclohexanone oxime. According to the system of the present invention, organic impurities can be more effectively removed by the purification steps, including extraction, stripping, adsorption by activated carbon, and so on. In addition, only a portion of the inorganic process solution is fed to the nitric acid absorption tower, in which, after being supplemented with nitric acid and adjusted in composition, this portion of the inorganic process solution is mixed with the residual portion of the inorganic process solution, and the resulting mixture is recycled back to the hydroxylamine formation zone for use in the hydroxylamine phosphate synthesis in the next cycle; thereby the loss rate of hydroxylamine due to degradation in the nitric acid absorption tower can be reduced.

EXAMPLE 1

An inorganic process solution, which contains phosphate salts, comprises 2.88 mol/kg or more of hydrogen ions, 2.68 mol/kg or more of phosphate salts, and 0.2 mol/kg or more of free nitric acid. The inorganic process solution was continuously fed to the hydroxylamine formation tower, in which hydroxylamine phosphate was synthesized by reducing nitrate with a hydrogen gas in the presence of a 10% Pd/activated carbon (Degussa Company, Japan) at a temperature of 53° C. and at a partial hydrogen pressure of 55%. The concentration of hydroxylamine phosphate in the inorganic process solution at the outlet of the hydroxylamine formation tower was 1.14 mol/kg.

The inorganic process solution containing hydroxylamine phosphate and the solution of cyclohexanone in toluene were continuously and respectively fed to the oximation tower via its top and bottom to perform oximation at a temperature of 51° C., in which the molar ratio of hydroxylamine to cyclohexanone was 0.90:1. The concentration of cyclohexanone oxime in the organic phase discharged from the top of the oximation tower was 33.1 wt. %.

The inorganic process solution discharged from the bottom of the oximation tower was delivered to an extraction tower, in which the inorganic process solution was extracted with toluene at a temperature of 70° C. After extraction, the inorganic process solution was discharged from the bottom of the extraction tower and delivered to a stripping tower. Stripping was then performed at a temperature of 130° C., thereby removing organic impurities having lower boiling points from the inorganic process solution. After stripping, the inorganic process solution contained 0.045 mol/kg of hydroxylamine phosphate and 0.0216 wt. % of total organic carbon.

The inorganic process solution after stripping was delivered to an activated carbon absorption tower, where organic impurities with high boiling points were removed by adsorption with activated carbon at a temperature of 20° C. The purified inorganic process solution contained 0.045 mol/kg of hydroxylamine phosphate and 0.0089 wt. % of total organic carbon.

The purified inorganic process solution was delivered to an adjusting zone, in which 12 v/v % of the total inorganic process solution was fed to a nitric acid absorption tower and supplemented with nitric acid there, and then mixed with the residual portion of the inorganic process solution. The mixture was recycled back to the hydroxylamine formation zone as the feed of the hydroxylamine formation tower. Analysis of the feed showed that only 0.005 mol/kg of hydroxylamine phosphate was degraded during the supplementation of nitric acid; therefore the loss rate of hydroxylamine phosphate is 0.44 mol %, based on the total moles of hydroxylamine phosphate in the system according to the present invention.

EXAMPLE 2

An inorganic process solution, containing phosphate salts, comprises 3.45 mol/kg or more of hydrogen ions, 3.05 mol/kg or more of phosphate salts, and 0.58 mol/kg or more of free nitric acid. The inorganic process solution was continuously fed to the hydroxylamine formation tower, in which hydroxylamine phosphate was synthesized by reducing nitrate with a hydrogen gas in the presence of a 10% Pd/activated carbon (Degussa Company, Japan) at a temperature of 53° C. and at a partial hydrogen pressure of 55%. The concentration of hydroxylamine phosphate in the inorganic process solution at the outlet of the hydroxylamine formation tower was 1.41 mol/kg.

The inorganic process solution containing hydroxylamine phosphate and a first portion of the solution of cyclohexanone in toluene were fed to a pre-mixing tank in the same direction. In the pre-mixing tank, both solutions were pre-mixed at a temperature of 37° C. and at a pressure of 1 atm to form a pre-mixed mixture. The concentration of hydroxylamine in the pre-mixed mixture at the outlet of the pre-mixing tank was reduced to 45% of its initial concentration.

The pre-mixed mixture was fed into the oximation tower from its top and a second portion of the solution of cyclohexanone in toluene was fed into the oximation tower from its bottom. The solutions entering from opposite directions contacted each other and were subjected to an oximation reaction at a temperature of 51° C., in which the molar ratio of hydroxylamine to cyclohexanone (total of the first portion and the second portion) was 0.90:1. The concentration of cyclohexanone oxime in the organic phase discharged from the top of the oximation tower was 38.4 wt. %.

The inorganic process solution discharged from the bottom of the oximation tower was delivered to an extraction tower, in which the inorganic process solution was extracted with toluene at a temperature of 70° C. After extraction, the inorganic process solution was discharged from the bottom of the extraction tower and delivered to a stripping tower. Stripping was performed at a temperature of 130° C., thereby removing organic impurities having lower boiling points from the inorganic process solution. After stripping, the inorganic process solution contained 0.062 mol/kg of hydroxylamine phosphate and 0.0248 wt. % of total organic carbon.

After stripping, the inorganic process solution was delivered to an activated carbon absorption tower, in which organic impurities with high boiling points were removed by adsorption with activated carbon at a temperature of 20° C. The purified inorganic process solution contained 0.062 mol/kg of hydroxylamine phosphate and 0.0113 wt. % of total organic carbon.

The purified inorganic process solution was delivered to an adjusting zone, in which 14 v/v % of the total inorganic process solution was fed to a nitric acid absorption tower and supplemented with nitric acid there, and then mixed with the residual inorganic process solution. The mixture was recycled back to the hydroxylamine formation zone as the feed of the hydroxylamine formation tower. Analysis of the feed showed that only 0.009 mol/kg of hydroxylamine phosphate was degraded during the supplementation of nitric acid; therefore, the loss rate of hydroxylamine phosphate was 0.63 mol %, based on the total moles of hydroxylamine phosphate in the system according to the present invention.

EXAMPLE 3

An inorganic process solution, containing phosphate salts, comprises 4.00 mol/kg or more of hydrogen ions, 3.27 mol/kg or more of phosphate salts, and 0.72 mol/kg or more of free nitric acid. The inorganic process solution was continuously fed to the hydroxylamine formation tower, in which hydroxylamine phosphate was synthesized by reducing nitrate with a hydrogen gas in the presence of a 10% Pd/activated carbon (Degussa Company, Japan) at a temperature of 53° C. and at a partial hydrogen pressure of 55%. The concentration of hydroxylamine phosphate in the inorganic process solution at the outlet of the hydroxylamine formation tower was 1.64 mol/kg.

The inorganic process solution containing hydroxylamine phosphate and a first portion of the solution of cyclohexanone in toluene were fed to a pre-mixing tank in the same direction. In the pre-mixing tank, both solutions were pre-mixed at a temperature of 37° C. and at a pressure of 1 atm to form a pre-mixed mixture. The concentration of hydroxylamine in the pre-mixed mixture at the outlet of the pre-mixing tank was reduced to 63% of its initial concentration.

The pre-mixed mixture was fed to the oximation tower from its top and a second portion of the solution of cyclohexanone in toluene was fed to the oximation tower from its bottom. The solutions entering from opposite directions contacted with each other and were subjected to an oximation reaction at a temperature of 51° C., in which the molar ratio of hydroxylamine to cyclohexanone (total of the first portion and the second portion) was 0.90:1. The concentration of cyclohexanone oxime in the organic phase discharged from the top of the oximation tower was 42.2 wt. %.

The inorganic process solution discharged from the bottom of the oximation tower was delivered to an extraction tower, in which the inorganic process solution was extracted with toluene at a temperature of 70° C. After extraction, the inorganic process solution was discharged from the bottom of the extraction tower and delivered to a stripping tower. Stripping was performed at a temperature of 130° C., thereby removing organic impurities having lower boiling points in the inorganic process solution. After stripping, the inorganic process solution contained 0.080 mol/kg of hydroxylamine phosphate and 0.0287 wt. % of total organic carbon.

After stripping, the inorganic process solution was delivered to an activated carbon absorption tower, in which organic impurities with high boiling points were removed by adsorption with activated carbon at a temperature of 20° C. The purified inorganic process solution contained 0.080 mol/kg of hydroxylamine phosphate and 0.0139 wt. % of total organic carbon.

The purified inorganic process solution was delivered to an adjusting zone, in which 17 v/v % of the total inorganic process solution was fed to a nitric acid absorption tower and supplemented with nitric acid there, and then mixed with the residual inorganic process solution. The mixture was recycled back to the hydroxylamine formation zone as the feed of the hydroxylamine formation tower. Analysis of the feed showed that only 0.014 mol/kg of hydroxylamine phosphate was degraded during the supplementation of nitric acid; therefore the loss rate of hydroxylamine phosphate was 0.85 mol % based on the total moles of hydroxylamine phosphate in the system according to the present invention.

The invention has been described using exemplary preferred embodiments. However, it is to be understood that the scope of the invention is not limited to the disclosed embodiments. On the contrary, it is intended to cover various modifications and similar arrangement. The scope of the claims therefore should be accorded the broadest interpretation so as to encompass all such modifications and similar arrangements.

What is claimed is:

1. A recycling system for hydroxylamine formation and oximation, comprising:
    (a) a hydroxylamine formation zone in which nitrate is reduced to hydroxylamine with a hydrogen gas in the presence of a catalyst in an inorganic process solution containing an acidic buffering agent;
    (b) an oximation zone in which hydroxylamine formed in the hydroxylamine formation zone and cyclohexanone are subjected to an oximation reaction to form cyclohexanone oxime;
    (c) a pre-mixing tank connecting the hydroxylamine formation zone and the oximation zone;
    (d) a purification zone in which organic impurities in the inorganic process solution are removed; and
    (e) an adjusting zone having a nitric acid absorption tower for supplementing nitrate ions to the inorganic process, wherein the inorganic process solution fed into the adjusting zone comprises a first portion that is fed to the nitric acid absorption tower, and a second portion that is not fed to the nitric acid absorption tower, such that the volume of the first portion of the inorganic process solution does not exceed 20% (by volume) of the total volume of the inorganic process solution, and in which the first portion of the inorganic process solution, after being supplemented with nitrate ions in the nitric acid absorption tower, is mixed with the second portion of the inorganic process solution.

2. The system according to claim 1, wherein the purification zone is provided with an activated carbon adsorption tank.

3. The system according to claim 1, wherein the purification zone further comprises an extraction tower.

4. The system according to claim 1, wherein the purification zone further comprises a stripping tower.

5. The system according to claim 1, wherein, in the pre-mixing tank, the inorganic process solution containing a high concentration of hydroxylamine phosphate is pre-mixed with a portion of the cyclohexanone, such that the concentration of hydroxylamine phosphate in the inorganic process solution is reduced to 80% or less of its initial concentration.

6. The system according to claim 5, further comprising a first delivery line for delivering the inorganic process solution containing the high concentration of hydroxylamine phosphate to the pre-mixing tank, and a second delivery line for delivering the cyclohexanone to the pre-mixing tank, whereby the inorganic process solution containing the high concentration of hydroxylamine phosphate and the cyclohexanone are delivered to the pre-mixing tank from the same direction.

* * * * *